(12) United States Patent
Prabhakarpandian et al.

(10) Patent No.: US 10,641,761 B2
(45) Date of Patent: May 5, 2020

(54) SYNTHETIC MICROFLUIDIC SYSTEMS FOR TUMOR METASTASIS

(71) Applicant: CFD Research Corporation, Huntsville, AL (US)

(72) Inventors: Balabhaskar Prabhakarpandian, Madison, AL (US); Kapil Pant, Huntsville, AL (US)

(73) Assignee: CFD Research Corporation, Huntsville, AL (US)

(*) Notice: Subject to any disclaimer, the term of this patent is extended or adjusted under 35 U.S.C. 154(b) by 268 days.

(21) Appl. No.: 15/898,035

(22) Filed: Feb. 15, 2018

(65) Prior Publication Data
US 2018/0172670 A1 Jun. 21, 2018

Related U.S. Application Data

(62) Division of application No. 14/202,511, filed on Mar. 10, 2014, now Pat. No. 9,933,413.
(60) Provisional application No. 61/775,158, filed on Mar. 8, 2013.

(51) Int. Cl.
| | |
|---|---|
| G01N 33/50 | (2006.01) |
| B01L 3/00 | (2006.01) |
| G01N 33/574 | (2006.01) |
| C12M 1/00 | (2006.01) |
| C12M 3/00 | (2006.01) |
| G01N 33/86 | (2006.01) |

(52) U.S. Cl.
CPC ..... *G01N 33/5029* (2013.01); *G01N 33/5005* (2013.01); *G01N 33/5011* (2013.01); *G01N 33/5061* (2013.01); *G01N 33/5088* (2013.01); *G01N 33/86* (2013.01); *B01L 3/5027* (2013.01); *G01N 2333/4703* (2013.01); *G01N 2333/70525* (2013.01)

(58) Field of Classification Search
CPC .......................... G01N 33/5029; B01L 3/5027
USPC .......................................................... 435/29
See application file for complete search history.

(56) References Cited

U.S. PATENT DOCUMENTS

| | | | |
|---|---|---|---|
| 5,601,997 | A | 2/1997 | Tchao |
| 7,725,267 | B2 | 5/2010 | Prabhakarpandian et al. |
| 8,175,814 | B2 | 5/2012 | Prabhakarpandian et al. |
| 8,355,876 | B2 | 1/2013 | Prabhakarpandian et al. |
| 8,380,443 | B2 | 2/2013 | Prabhakarpandian et al. |
| 8,417,465 | B2 | 4/2013 | Prabhakarpandian et al. |
| 8,589,083 | B2 | 11/2013 | Prabhakarpandian et al. |
| 2003/0021457 | A1 | 1/2003 | Kirk et al. |

(Continued)

FOREIGN PATENT DOCUMENTS

WO 2014/085498 A1 6/2014

*Primary Examiner* — Kevin Joyner
*Assistant Examiner* — Holly Kipouros
(74) *Attorney, Agent, or Firm* — Maschoff Brennan; Jonathan M. Benns

(57) ABSTRACT

A method of assaying metastasis can include: providing a device of one of the embodiments; introducing the at least one cancer cell into the at least one internal chamber or at least one fluid channel; and studying metastasis of the at least one cancer cell. Optionally: introducing cancer cells into a first internal chamber; detecting escape of the cancer cell from the first internal chamber into the fluid channel; detecting migration of the cancer cell through the fluid channel; detecting adhesion of the cancer cell to a coating on the fluid channel; detecting invasion of the cancer cell into a second internal chamber from the fluid channel; or visualizing metastasis of the cancer cell with a visualization device.

20 Claims, 11 Drawing Sheets

(56) References Cited

U.S. PATENT DOCUMENTS

| | | |
|---|---|---|
| 2006/0154361 A1 | 7/2006 | Wikswo et al. |
| 2010/0099136 A1 | 4/2010 | Prabhakarpandian et al. |
| 2010/0227312 A1 | 9/2010 | Pant et al. |
| 2011/0104658 A1 | 5/2011 | Prabhakarpandian et al. |
| 2013/0101991 A1 | 4/2013 | Prabhakarpandian et al. |
| 2013/0149735 A1 | 6/2013 | Prabhakarpandian et al. |
| 2014/0057311 A1 | 2/2014 | Kamm et al. |

SYNTHETIC MICROFLUIDIC SYSTEMS FOR TUMOR METASTASIS

CROSS-REFERENCE

This patent application is a divisional of U.S. patent application Ser. No. 14/202,511 filed Mar. 10, 2014, which claims priority to U.S. Provisional Application No. 61/775,158 filed Mar. 8, 2013, which applications are incorporated herein by specific reference in their entirety.

BACKGROUND

Cancer continues to be a serious illness even though it has been a center of research for a long time. Tumors can be classified as benign (e.g., non-cancerous and normally don't spread) or malignant (e.g., cancerous that can spread to different parts of the body). Cancer can spread to different parts of the body via two different mechanisms: (1) invasion; and (2) metastasis. Invasion involves direct migration and penetration by cancer cells into adjacent tissues, whereas metastasis refers to cancer cells penetrating into circulation (e.g., lymphatic and blood vessels) followed by invasion of normal tissue somewhere else in the body. That is, metastasis results in additional secondary tumors away from the original, primary tumor location. This allows cancer to spread to almost anywhere in the body. The complex process of metastasis can be broken into four individual steps: (1) Breakup of tumor cells from original site and migration into the circulatory system; (2) Attachment of circulating tumor cells to the vessel walls; (3) Migration of tumor cells from vessel into tissue; and (4) Invasion of tumor cells forming new colonies.

Metastatic cells break away from the other cells in the tumor, and overcome constraints on cell movement imposed by the basement membrane and other barriers. Tumor cells often secrete proteases that help the tumor cells digest the basement membrane and invade into the extracellular matrix, which can be followed by release into circulation. Commonly, the ability of a tumor cell to invade the matrix is taken to be indicative of its metastatic nature. However, the process of cancer metastasization in vivo is more complex and only a few of the tumor cells form metastatic tumors. In order to metastasize, the cells first have to survive circulation, adhere to the vessel wall and migrate/invade into normal tissue to form new colonies. Usually, the host immune response or high shear zones are likely to destroy tumor cells in circulation. Furthermore, only a fraction of the circulating metastatic cells adhere to the vessel wall, potentially using several different mechanisms. For example, studies show that these tumor cells in the circulation often utilize the presence of leukocytes to enhance adhesion and extravasation. Cell adhesion prior to migration is dependent upon the microenvironment including geometric features of the vasculature and the associated local hemodynamic factors such as wall shear stress, dynamic pressure, and residence time in circulation. Thus, accurate characterization of metastasis involves representation of adhesion and circulation, in addition to migration or invasion.

Adhesion of tumor cells to the endothelium is hypothesized to occur by two potentially very different mechanisms. According to the first hypothesis, tumor cells are trapped in capillaries based on vessel-size restriction. The second theory argues that tumor cells can adhere to endothelium by forming shear-resistant bonds with the endothelium. Basic cellular adhesion process has been well studied over the past two to three decades for the development of both static and fluidic assays. The process of adhesion involves rolling of cells on the endothelium, mediated by selectins, followed by a firm adhesion process mediated by integrins.

Previously, researchers have been studying particle adhesion on the endothelium using idealized straight channels under fluidic conditions. However, these devices lack correspondence with in vivo geometry, scale/aspect ratios (e.g., microvasculature vs. large vessel models), large reagent volumes, and are inadequate in studying adhesion event differences between healthy and diseased vasculature.

After a tumor cell has adhered to the walls of the endothelium, it can start the process of migration/invasion into the tissue using gaps in the endothelium. There are currently several in vitro methods that study cell migration that can be classified as 2-D or 3-D cell migration models. 2-D models are easy to set up and run, but do not represent the microenvironment of living tissues and the migration is unidirectional. 3-D models, on the other hand, are difficult to set up, but can be used to mimic the microenvironment using extracellular matrix components. The classical way to study 2-D cell migration is the use of a two-chamber system commonly known as the Boyden chamber or the transwell assay. It consists of a porous membrane separating two chambers and the cell migration from one chamber to another in the presence of a chemical signal (chemoattractant). Several companies have adapted this format for high throughput analysis using 96 and 384 well plate formats. A major problem with the Boyden chamber is the inability to visualize cells during migration. In addition, the end point measurement involves staining procedures, which are tedious and allow for inaccurate assessment of the migrated cells.

Recent modifications to this technique such as the Dunn chamber have allowed direct viewing of the cell migration but have also posed new problems with the study being performed over long annular (1 mm) distance. Incorporation of shear flow in these filter assays, while possible, is inefficient due to the large reagent volumes needed. The large fluid volumes also render the system inaccurate as they cause membrane fluctuation, which leads to strong disturbances in set shear conditions.

A recent entry to the field, μ-Slide chemotaxis assay from Ibidi, LLC (Verona, Wis.) consists of linear channels allowing real-time microscopy. However, the migration takes place under static conditions and cells migrate along a linear path with no obstructions (filters, etc.). In addition this device is a 2-D device and is not amenable to studies on suspension cells. From among all these devices, the Boyden chamber is still the most commonly used device.

Therefore, there remains a need in the art for a better system and methodology for studying tumor metastasis.

BRIEF DESCRIPTION OF THE FIGURES

The foregoing and following information as well as other features of this disclosure can become more fully apparent from the following description and appended claims, taken in conjunction with the accompanying drawings. Understanding that these drawings depict only several embodiments in accordance with the disclosure and are, therefore, not to be considered limiting of its scope, the disclosure can be described with additional specificity and detail through use of the accompanying drawings, in which:

DETAILED DESCRIPTION

Figure 1A:
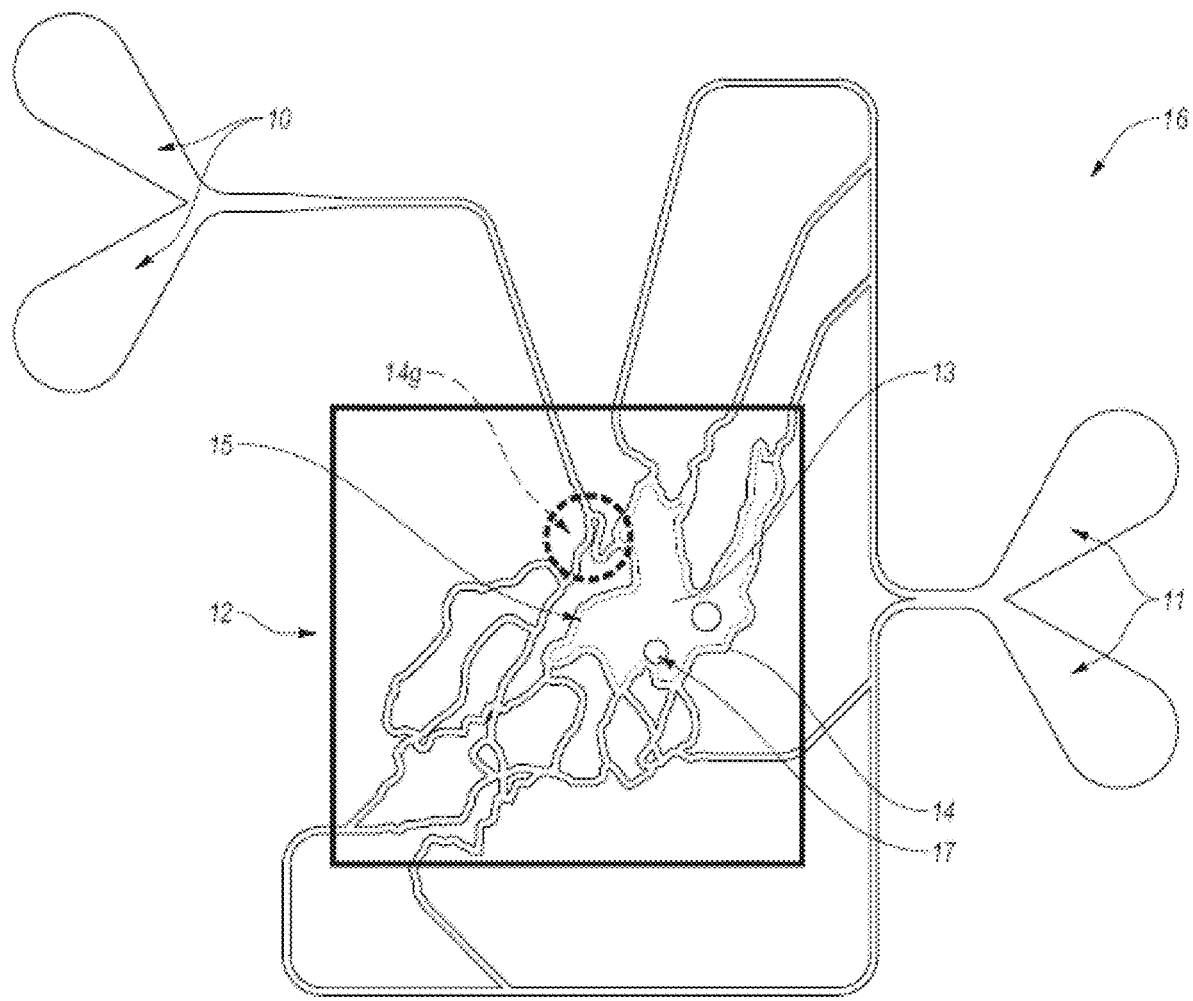
FIG. 1A illustrates an embodiment of a device having a plurality of tissue spaces connected by a plurality of fluid channels.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It can be readily understood that the aspects of the present disclosure, as generally described herein, and illustrated in the figures, can be arranged, substituted, combined, separated, and designed in a wide variety of different configurations, all of which are explicitly contemplated herein.

Generally, the present invention includes a device and methodology to study and characterize tumor cell metastasis in physiologically realistic microenvironments (e.g., MIcrofluidic MEtastatic Assay or MIME). The device and methodologies can also be used to study targeted therapy to tumor cells and to inhibit metastasis. The device is configured with an internal chamber and surrounding capillary channels to simulate the cancer metastasis multi-step process. The device can include an internal chamber as a tissue chamber, which can contain at the start of an assay with the cancer cells in the tissue chamber and then leaving the tissue chamber and migrating to distant parts of the fluidic channels of the device via the capillary channels that mimic the bloodstream or the lymphatic system. The device and methodologies allow for the study and visualization in real time of: cancer cells breaking of the extracellular matrix in the tissue chamber and simulating metastatic tumor cells, cancer cells escaping into the circulatory system of the microfluidic pathway; adhesion of cancer cells to the vascular wall at remote locations by adhering to endothelial cells cultured in the microfluidic channels of the device; and by migration/invasion of the cancer cells into other tissue chambers and subsequent proliferation in the tissue chambers (with or without other cells in the invaded tissue chamber). The device and methodologies provide for an environment to facilitate studying the interplay between these cellular activities, and can provide for a platform for developing therapeutics for both cancer and inflammatory/autoimmune diseases. The device provides a platform to study the complexity of the metastasis phenomena in vivo. The device can be used as an in vitro model to provide reproducible and screen-friendly approach to developing new therapies against cancer and cancer metastasis.

In one embodiment, the configuration of the device allows for studying the multi-faceted metastatic process with a realistically modeled in vitro system that can be used to analyze cell migration and distal invasion. The internal chamber and capillary channels provide for dynamic incubation chambers to study cell migration and invasive potential under the influence of different chemoattractant gradients. The device can also be configured to: (a) reproduce physiological features of an appropriate microenvironment for simulated fluid shear and size/topology; (b) allow for analysis and visualization for the entire metastatic process from breaking away to invasion by cancer cells that can be quantitative; (c) provide real-time visualization of cell migration, attachment, and invasion; and (d) allow studies to be simple with high throughput.

The internal chamber surrounded by capillary fluid channels provides an integrated microfluidic metastatic device for investigating the metastatic potential of a tumor cell in a physiologically realistic microenvironment. The device can include an optically transparent or transmissive plastic body that is disposable with an in vivo realistic microcirculatory network (e.g., 10-100 um size range) with a complex fluid channel network morphology including branching and loops and a simulated vascular wall with an endothelial layer growing thereon. The device can be a microfluidic chip that mimics in vivo geometries, which can be used to study the metastasis phenomena and particle/cell adhesion on the endothelium. The developed chip allows for detailed understanding of differential adhesion of cells in a metastatic environment.

Figures 1B, 1C:
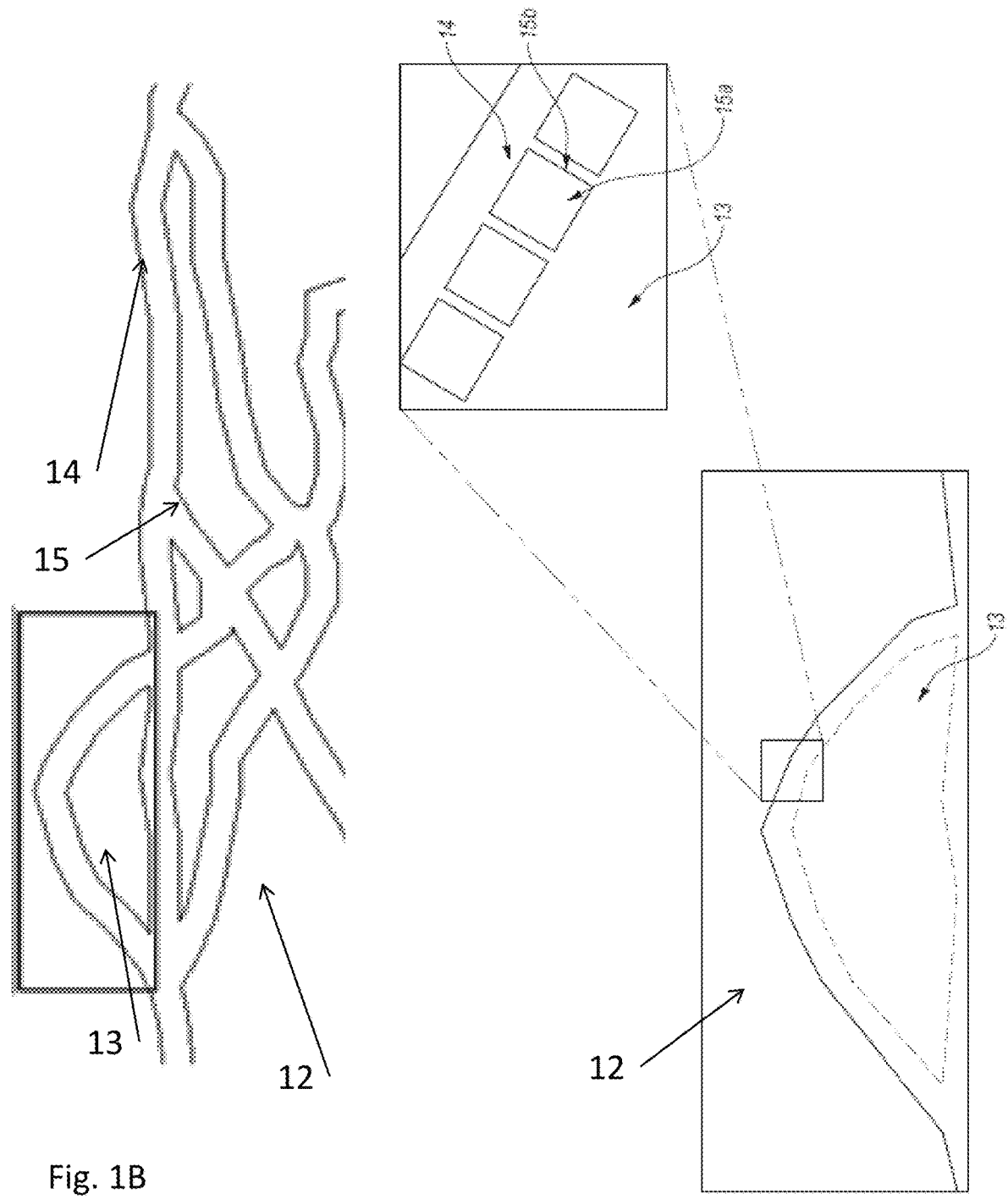
FIG. 1B illustrates a section of an embodiment of a device having a plurality of tissue spaces connected by a plurality of fluid channels.
FIG. 1C illustrates an embodiment of a porous wall that separates a tissue space and fluid channel of a device, where the wall fluidly couples the tissue space and fluid channel.
Figure 1D:
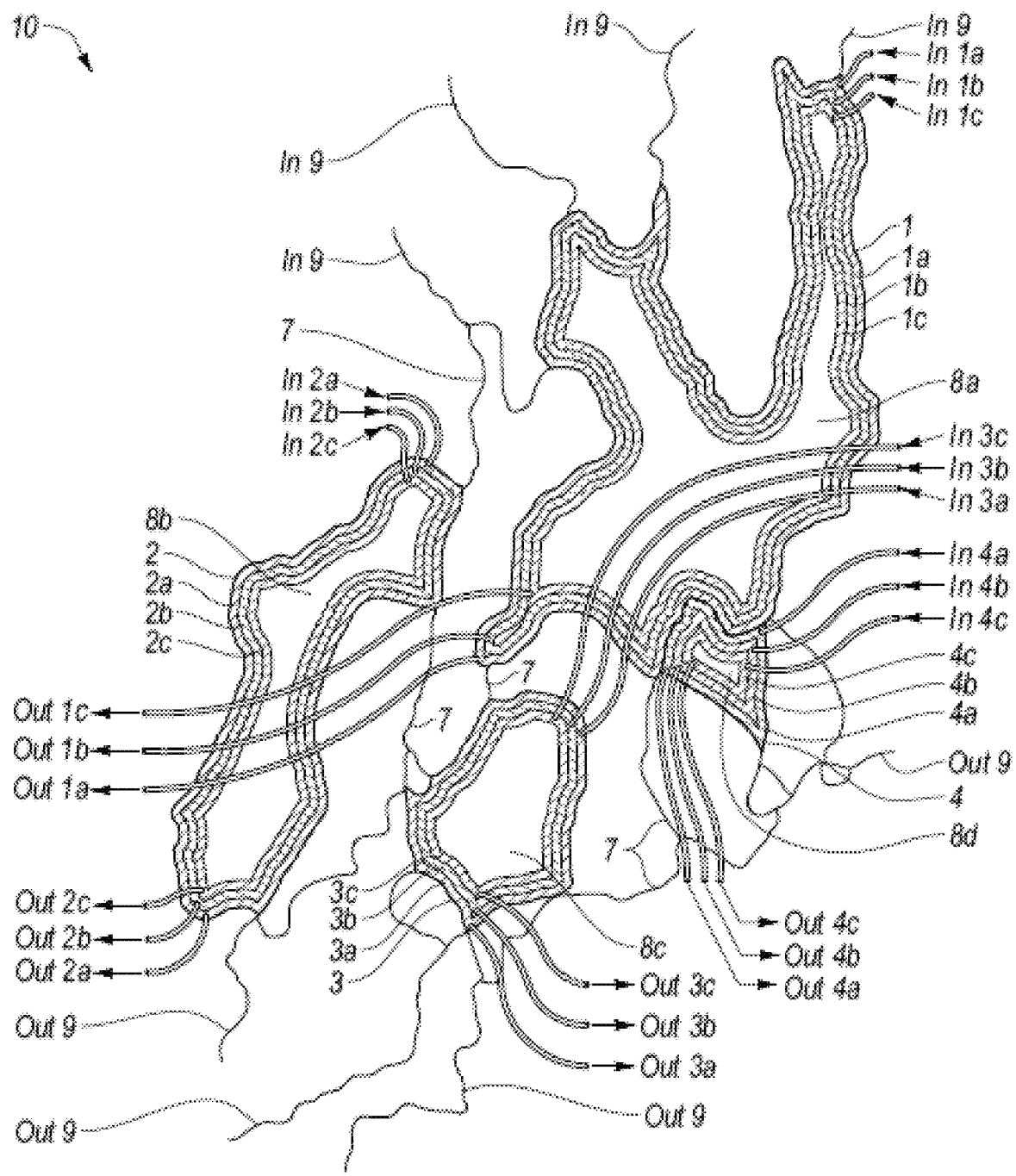
FIG. 1D illustrates an embodiment of a device having a plurality of tissue spaces connected by a plurality of fluid channels in a multi-channel orientation.

FIGS. 1A-1D illustrate an embodiment of a device 16 having a synthetic microvascular network (SMN) 12 comprising an internal chamber (e.g., extravascular tissue space) surrounded by fluid microchannels (e.g., capillaries and lymphatic channels). However, the device can be an idealized microvascular network (IMN). SMN and IMN are known terms in the art. An embodiment of the SMN 12 can include realistic flow channels 14 with realistic features 14g and tissue spaces 13, as shown in FIGS. 1B-1D. The tissue space 13 and capillary network are irregular. Here, the wall of a flow channel (e.g., capillary channel) separating the flow channel lumen from the lumen of the tissue space 13 is shown in detail to show the pillars 15a and gaps 15b. In this embodiment, one wall of the nonlinear flow channel 14 is constructed such that portions of the wall contain gaps 15b located between portions of the wall, called pillars 15a (or posts, islands, etc.), which may be configured to provide gaps 15b of various selected sizes. For fabrication of the SMN 12 comprising the extravascular (extra-flow channel) tissue space 13, CAD drawings of a physiological network are modified to include gaps 15b with desired gaps or pores in the walls of the vessels. The patterns of these vessels include tissue sections comprising a portion of or the entire physiological tissue space. The lumens of the tissue spaces shown in FIGS. 1B-1C may comprise posts, pillars, or other structures made of plastic substrate to facilitate the growth of adhesion-dependent cells. The SMN 12 can include inlet ports 10 and outlet ports 11. The tissue space may also include inlet/outlet ports 17. Any area surrounded by the flow channels 14 can be the tissue space 13.

The device can be comprised of a clear plastic, such as PDMS, and modeled after vascular networks. The CAD drawings of the networks can be modified using AutoCAD LT to include 8-μm gaps at the walls of the channels and internal chambers. The size of the "structures" or "islands" (see FIGS. 1B-1C) introduced in the walls as a result of these gaps is the single most critical element of the network topology modifications.

The device can be fabricated with PDMS, and the size of these structures can be configured to represent different tissues and different disease states. In one example, the structures can be 50×50 μm in size. The modified network topology can be analyzed via high-fidelity computational modeling. The analyzed network can be fabricated using conventional soft lithography/replica casting techniques, such as those described herein.

The provisional application shows that two capillary channels can be separated by a wall having 50-micron-wide slits. As such, the devices can include central chambers surrounded by at least two adjacent capillary channels. In view of the SMN of FIGS. 1A-1C, a corresponding SMN modeled after live physiology with at least two capillary channels would look like FIG. 1D. FIG. 1D illustrates an embodiment of SMN network having SMN fluid pathways and SMN multi-chambered cell culture constructs.

FIG. 1D illustrates a SMN 10 having one of more fluid inlets In 9 and one or more fluid outlets Out 9 with one or more multi-channel constructs 1, 2, 3, 4, each having central chambers 8a, 8b, 8c, 8d (e.g., while four multi-channel constructs are shown, any integer can be used). The multi-channel constructs 1, 2, 3, 4 can be configured with inlets and outlets in accordance with any of the embodiments or figures described herein. Also, while shown to be SMN, the configuration can be an IMN. The SMN can be configured with any number of fluid pathways 7 linking the multi-channel constructs, which can be in any manner, and which SMN can be designed via simulation of real biological or artificial fluid pathways.

As shown, multi-channel construct 1 can include a central chamber 8a surrounded by an outer conduit layer 1a (e.g., outer capillary channel) with barrier layer channels 1b, 1c therebetween. The outer conduit layer 1a can be fluidly coupled with the inlet In 9 and the outlet Out 9. Also, the outer conduit layer 1a can include an inlet In 1a and an outlet Out 1a. The barrier layer channels 1b, 1c can include inlets In 1b, In 1c and outlets Out 1b, Out 1c, respectively. While not shown, the central chamber 8a can include inlets or outlets, or it can receive content from the barrier layer channel 1c.

As shown, the multi-channel construct 2 can include a central chamber 8b surrounded by an outer conduit layer 2a (e.g., capillary channel) with barrier layer channels 2b, 2c therebetween. The outer conduit layer 2a can be fluidly coupled with the inlet In 9 and the outlet Out 9. Also, the outer conduit layer 2a can include an inlet In 2a and an outlet Out 2a. The barrier layer channels 2b, 2c can include inlets In 2b, In 2c and outlets Out 2b, Out 2c, respectively. While not shown, the central chamber 8b can include inlets or outlets, or it can receive content from the barrier layer channel 2c.

As shown, multi-channel construct 3 can include a central chamber 8c surrounded by an outer conduit layer 3a (e.g., outer capillary channel) with barrier layer channels 3b, 3c therebetween. The outer conduit layer 3a can be fluidly coupled with the inlet In 9 and the outlet Out 9. Also, the outer conduit layer 3a can include an inlet In 3a and an outlet Out 3a. The barrier layer channels 3b, 3c can include inlets In 3b, In 3c and outlets Out 3b, Out 3c, respectively. While not shown, the central chamber 8a can include inlets or outlets, or it can receive content from the barrier layer channel 3c.

As shown, multi-channel construct 4 can include a central chamber 8d surrounded by an outer conduit layer 4a with barrier layer channels 4b, 4c therebetween. The outer conduit layer 4a can be fluidly coupled with the inlet In 9 and the outlet Out 9. Also, the outer conduit layer 4a can include an inlet In 4a and an outlet Out 4a. The barrier layer channels 4b, 4c can include inlets In 4b, In 4c and outlets Out 4b, Out 4c, respectively. While not shown, the central chamber 8d can include inlets or outlets, or it can receive content from the barrier layer channel 4c. For example, a cancer cell can leave one chamber and travel through the fluid channels to a different chamber of the same network or tissue chamber of a different network in communication via the circulatory network, which can be studied with the present invention.

Figure 1E:
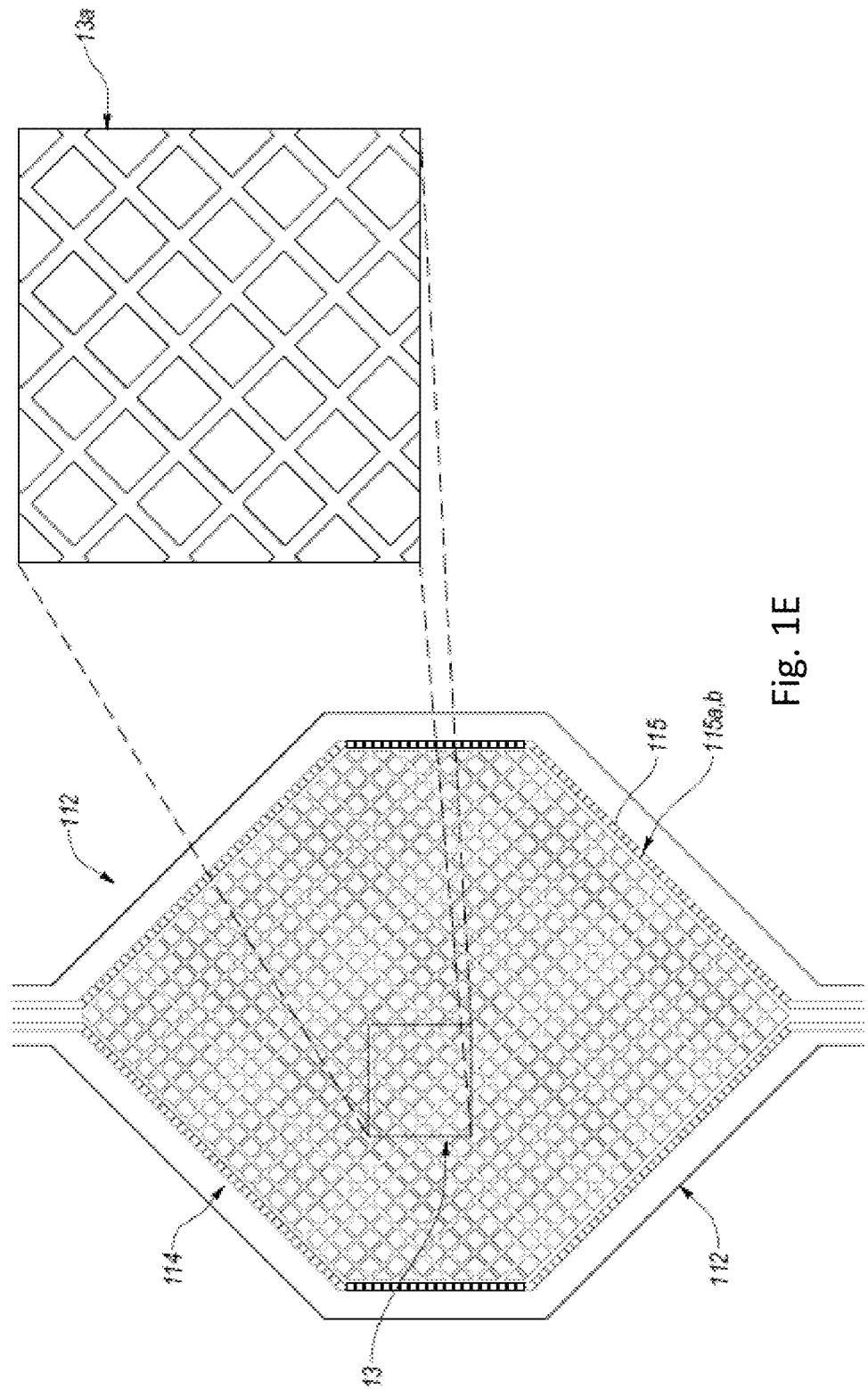
FIG. 1E illustrates an embodiment of an idealized microvascular network.

FIG. 1E shows a portion of an idealized microvascular network IMN 112 in a microfluidic chip. The IMN 112 comprises the idealized extravascular tissue space 13 surrounded by linear flow channels 114. Walls 115 separating the tissue space 13 from the linear flow channels 114 are permeable to aqueous buffers and are formed by plastic structures 115b separated by gaps 115a that range in size from 0.2 μm to 5 μm. Alternatively, the walls 115 may be made liquid permeable by way of pores in the wall that are from 0.2 μm to 30 μm in diameter. The extravascular tissue space 13 contains posts 13a (e.g., pillars) configured to facilitate the growth of adhesion-dependent cells to form a three-dimensional solid mono- or co-tissue culture or tumor. The posts 13a can be included in any vascular fluid flow path or extravascular space in any of the microfluidic chips. The posts 13a distribution, amount or arrangement or shape. Also, the tissue space 13 can be devoid of the posts 13a.

Figure 1F:
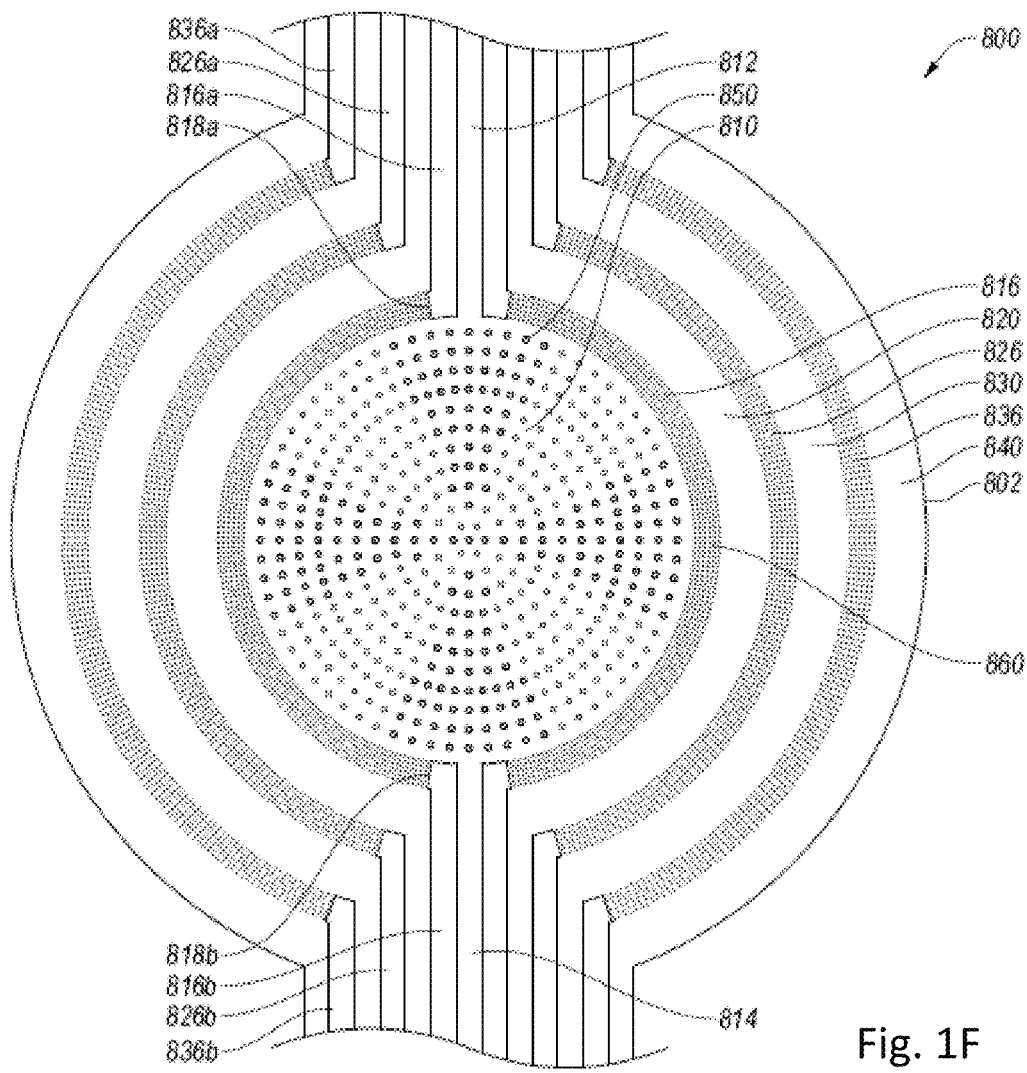
FIG. 1F illustrates an embodiment of an idealized microvascular network.

FIG. 1F shows another embodiment of a multi-channel structure 800 in accordance with the principles of the present invention. Here, the walls are made of the series of pillars in accordance with FIG. 5. The multi-channel cell culture device 800 is shown to include an internal chamber 810, an inner boundary layer channel 820, an outer boundary layer channel 830, and an outer conduit layer channel 840. However, only one boundary layer channel or more than two additional boundary layer channel can be located between the internal chamber 810 and outer conduit layer channel 840. The internal chamber 810 can include a fluid inlet 812 and a fluid outlet 814. The inner boundary layer channel 820 can include at least one fluid inlet and at least one fluid outlet as described herein. The outer boundary layer channel 830 can include at least one fluid inlet and at least one fluid outlet as described herein. The outer conduit layer channel 840 can include at least one fluid inlet and at least one fluid outlet as described herein. The internal chamber 810 can be defined by a porous tissue chamber wall 816, the inner boundary layer channel 820 can be defined by the porous tissue chamber wall 816 and a porous boundary layer wall 826, the outer boundary layer channel 830 can be defined by the porous boundary layer wall 826 and a porous outer conduit wall 836, and the outer conduit layer channel 840 is defined by the porous outer conduit wall 836 and an external wall 802 that is not porous. Here, the porous walls 816, 826, 836 can include a plurality of posts 860 that form the walls with the gaps between the posts 860. The porous walls 816, 826, 836 have one or more posts 860 laterally or radially oriented to form the walls.

In one embodiment, any of the chambers/conduits can include structure posts 850 that can be used to provide structure between top walls and bottom walls. The structure posts 850 can be coupled to a bottom wall, and may be coupled to a top wall when integrated with the side walls. Also, the top wall as a lid can rest on the structure posts 850. The structure posts can be used for cell culture, and can result in a higher cell density for organ simulations. FIG. 8 shows the central chamber 810 as having the posts 850, but it can be devoid of posts. Any of the boundary channels 820, 830 can include the posts 850 or be devoid of posts. The outer channel 840 can include the posts 850 or be devoid of posts.

Figure 1G:
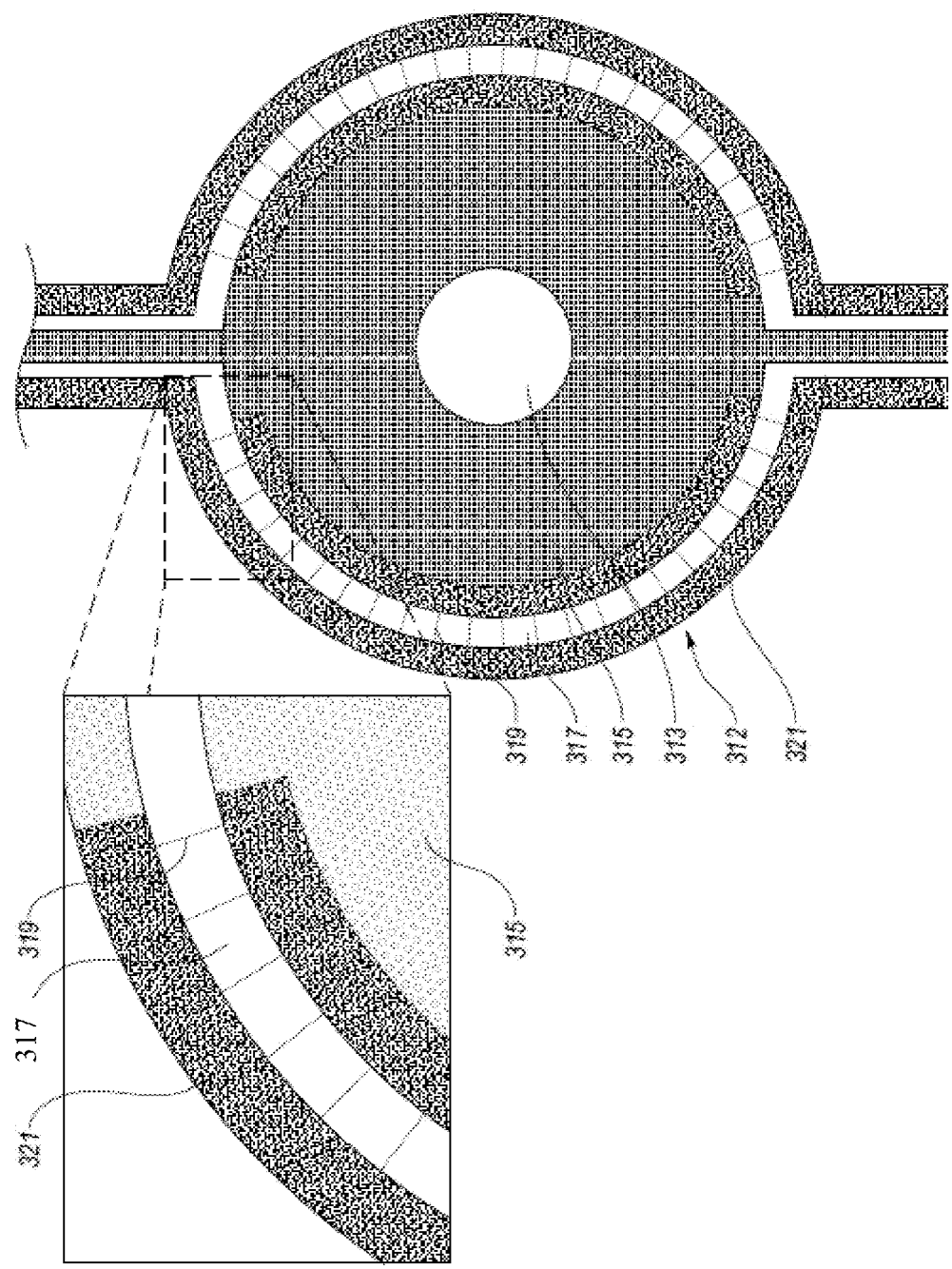
FIG. 1G illustrates an embodiment of an idealized microvascular network.

FIG. 1G shows a round IMN 312 in a microfluidic chip. The IMN includes a round tissue space 313 surrounded by a barrier space 315, which is surrounded by a wall 317 having gaps 319, and where an outer capillary channel 321 is on the outside. As shown, the barrier space 315 can include posts or pillars for cell culturing tissue.

Figure 5:
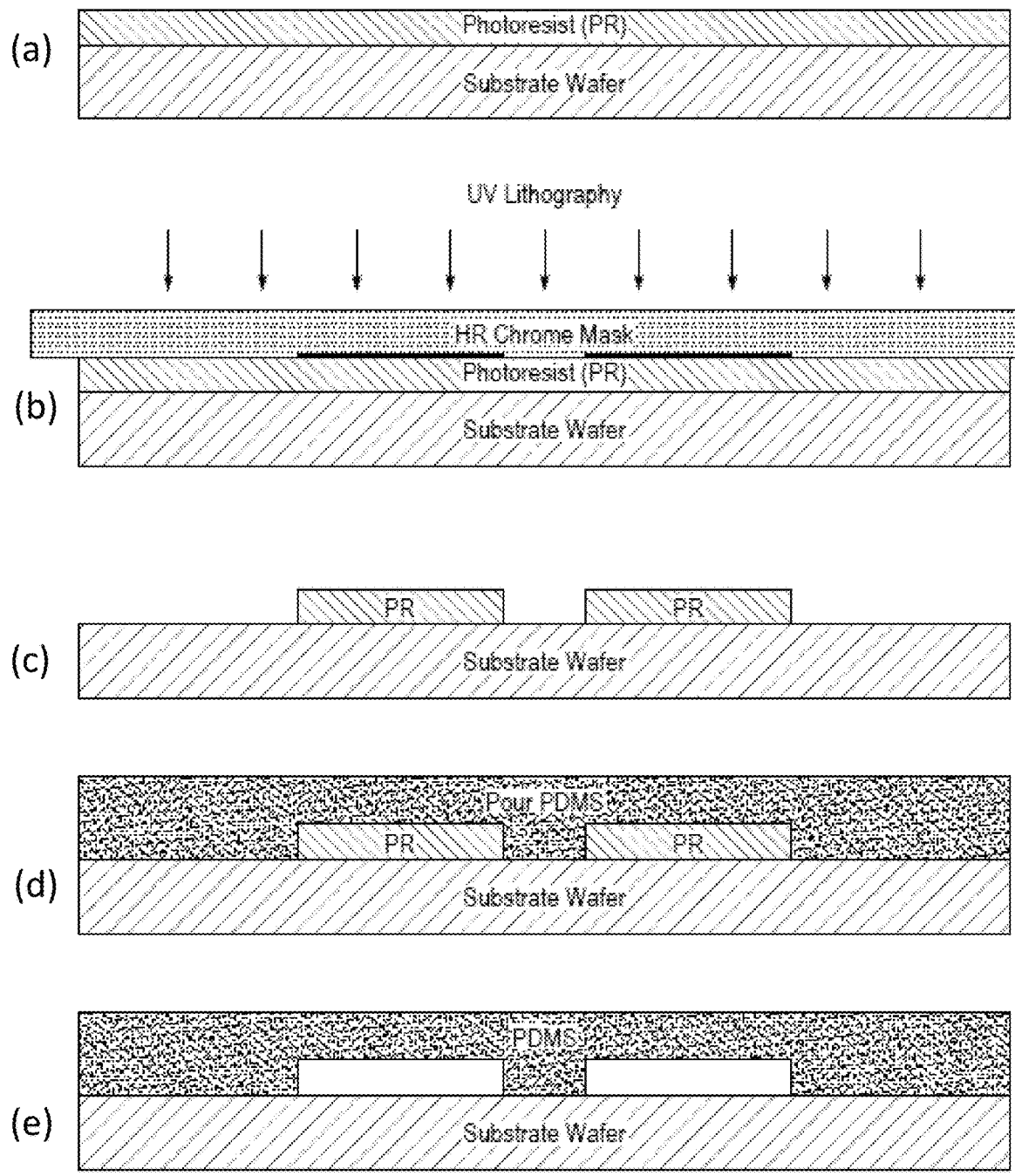
FIG. 5 illustrates steps (a)-(e) of a method of manufacturing a cell culture device.

The device can be fabricated with PDMS using conventional soft lithography (see FIG. 5). CAD drawings of the device can be developed to include post structures with gaps to act as paths for diffusion of fluid (e.g., nutrients or oxygen) into the central cell chamber. The CAD drawings can also be converted into a computational domain for simulational analysis. Briefly, the steps involved in the fabrication process shown in FIG. 5 include: (a) Spin-coating of photoresist (PR); (b) UV photolithography of the PR; (c) Development of the PR; (d) PDMS casting over developed PR, followed by PDMS curing; and (e) PDMS bonding to a cap (e.g., microscope slides, coverslip, glass, etc.). The devices can be tested visually for structural and fluidic integrity using fluorescent dyes. Fabrication of microfluidic devices from PDMS can be modulated to vary the widths, depths, PDMS concentration, and baking time.

Additional methods can be used for preparing the devices, such as the following example. The AutoCAD designs can be printed at high resolution on high-quality chrome masks (spot size of 0.25 μm with a minimum feature resolution of 1 μm. The chrome masks can be used for UV patterning of the desired thickness of positive resist spun on top of a silicon wafer. Silanization via the use of an adhesion promoter (Hexamethyldisilazane, HMDS) canl be used to enhance the strength of bonding of the photoresist to the silicon wafer. Sylgard 184 PDMS (Dow Corning, Midland, Mich.) can be poured over developed photoresist to generate complementary microchannels in PDMS. The PDMS can be cured at 60° C. for four to six hours in an oven, following which the PDMS can be peeled off from the master. Through holes, defining the inlets and outlets, can be punched using a beveled 25-gauge needle. The bonding surfaces of the PDMS and a pre-cleaned (ultrasonicated) glass slide/wafer can be bonded following oxygen plasma treatment. Tygon Microbore tubing with an outside diameter of 0.03" and inner diameter of 0.01" connected to 25- to 30-gauge stainless steel needle can be used for world-to-chip interfacing. The completed device can be sterilized by autoclaving at 121° C. for 15 minutes and stored in sterile environment until usage. The finished devices can be tested visually for structural integrity, particularly paying attention to the post structures. The fluidic integrity of the ports and PDMS/glass slide seal can be verified at the operational flow rates.

Various devices and configurations can be obtained in accordance with the invention, with a central chamber size ranging from 100 μm to 10 mm, surrounded by capillary channels of width 5 μm to 500 μm and height of 5 μm to 500 μm, separated by posts of 5 μm to 500 μm with gaps of 500 nm to 50 μm.

In one example, the device can include a ~1-mm sized central chamber surrounded by ~20-μm capillary channels with a depth of ~100 Posts separating the chambers can be ~50-μm wide with ~1-μm gaps. The provisional application shows an SEM image of two channels joined by ~50-μm long slits fabricated with PDMS using conventional soft lithography techniques. Also, the gaps can be as small as 500 nm. By comparing the yield and performance of different gap sizes in devices, tradeoffs between gap size and assay performance can be studied in these devices.

Figure 2:
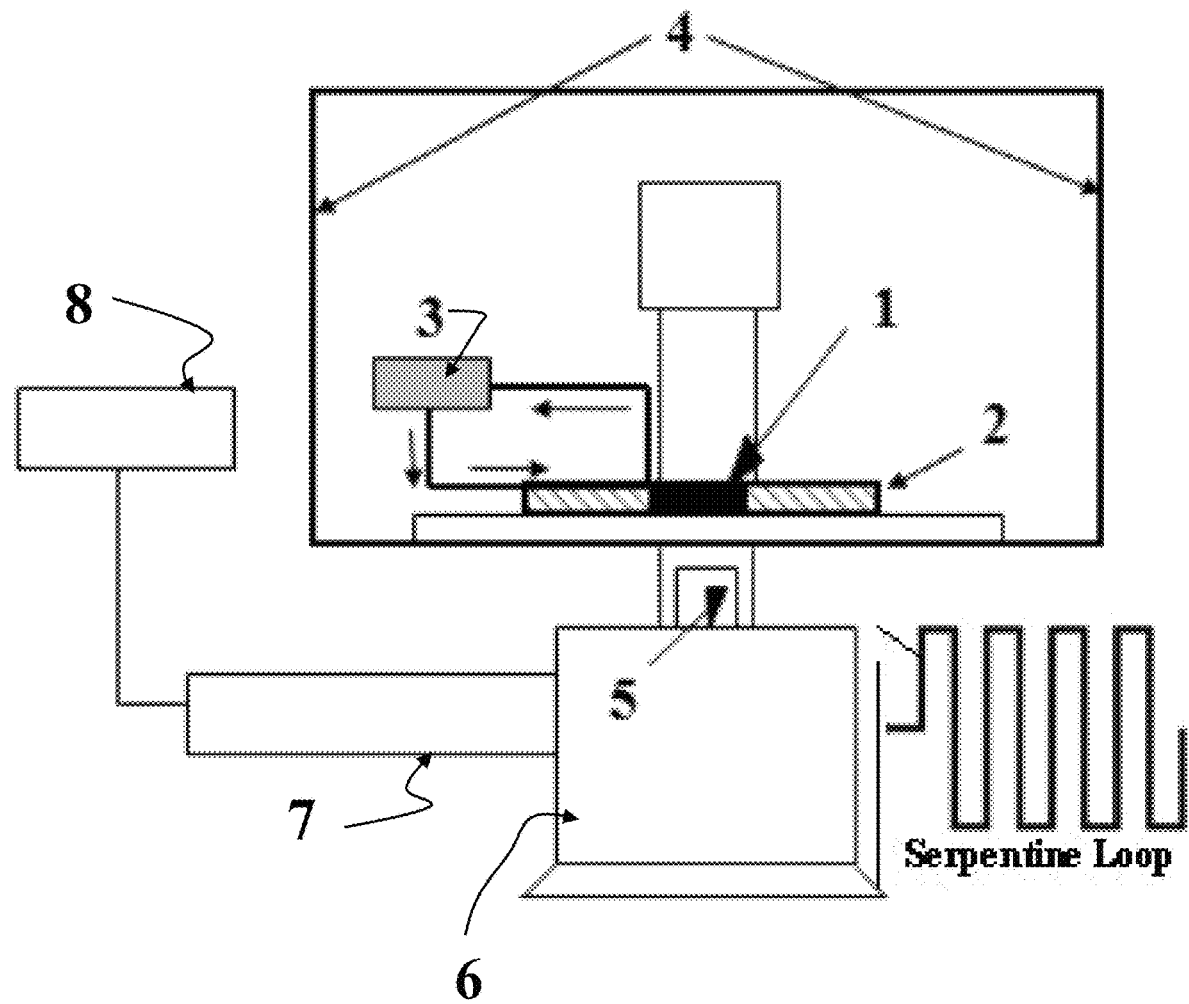
FIG. 2 illustrates a system that can utilize the devices of the invention.

FIG. 2 shows a drawing showing the components of a system used for screening tumor metastasis. The system shows a non-limiting example of a system for performing tumor drug delivery vehicle screening assays according to the present invention. The system comprises a pumping means (3) such as a peristaltic pump (for recirculation/multiple pass) or a syringe pump (single pass) to move fluids through microfluidic channel networks. For experiments with a peristaltic pump, a microfluidic chip (1) is placed on an automated stage device (2) and connected to a pump (3) that is connected to inlets, outlets, and, optionally, ports on the microfluidic chip (1). The microfluidic chip (1) is preferably contained within an incubation chamber (4) and is positioned over an objective lens (5) of a brightfield, phase contrast, or fluorescent microscope (6). Optical means such as a CCD camera or video camera (7) are used to visualize cells within the microfluidic chip (1). The camera (7) is in communication with a computer (8) for data collection and control of the microscope (6), the camera (7), and the microscope-mounted accessories. For experiments with a syringe pump, the syringe pump (3) is connected to the microfluidic chip (1) and fluid leaving the microfluidic chip (1) is sent to waste (not shown).

The system of FIG. 2 can be used in assays to study the effect of shear flow, as seen in vivo, on the survival rate of the tumors or cells in the metastasis. The device can be used even when the few cells that escape from the primary tissue space site and adhere, migrate, and invade other tissues forming secondary tumor colonies in other tissue spaces of the device. The cells in the device can be either destroyed by the host immune response or by local high shear zones, where the device can simulate physiological conditions by application of immune cells and shear zones in the channels. Although the host immune response is a complex phenomenon, the impact of critical elements on metastasis can be investigated by the careful introduction of targeted antibodies and macrophages (e.g., immunological substances) into the device. High shears are often found in diseased microvascular networks and their effect on metastasis can be readily studied in the environment provided by the device. Since the shear rates in the network vary significantly depending upon the location, the effect of shear using constant cross-sectional channel with set, constant shear rates can be performed with the device.

Accordingly, the device can be configured to study: (1) Breakup of tumor cells from original site and migration into the circulatory system; (2) Attachment of circulating tumor cells to the vessel walls; (3) Migration of tumor cells from vessel into tissue; and (4) Invasion of tumor cells forming new colonies.

In one embodiment, the vascular walls can contain gaps (e.g., 5-15 μm, coated with and without extracellular matrix) to mimic pores that can allow migration and invasion of metastatic cells into interstitial tissue space. The device can resolve and allow for the direct assessment of the cancer cells during metastasis, including viability in circulation, adhesion to endothelial cells, and migration/invasion into the extravascular tissue space. Accordingly, the device can include: a plastic microfluidic chip with morphology based on images of in vivo microcirculatory networks embedded with 5- to 15-μm leaky gaps; use in protocols for culturing of tumor cells, both metastatic (e.g., MDA-MB-231) and non-metastatic (e.g., MCF-7), in the network; use with automated protocols for real-time visualization and quantitation of metastasis including cell adhesion, migration, and circulation. The device can be used to study differences in endothelial adhesion and migration/invasion of both metastatic and non-metastatic cells under different flow conditions and in the presence or absence of extracellular matrix (e.g., matrigel). The device can be used to measure cell viability in circulation loop, location and extent of tumor cell adhesion, and rate of tumor cell migration or invasion into tissue space. The device can be used for drug screening applications using a nanopolymeric vehicle in circulation for delivery of drugs or inhibitory siRNA to tumor cells. GFP fluorescent tags can be used for such screening.

The device can be used to study circulating metastatic cell adhesion and extravasation, in both presence and absence of matrices (e.g., matrigel). As such, a tumor-specific microvasculature can be obtained from in vivo features using a rat dorsal skin model and rendering the model as a SMN on a microfluidic chip. The device can be used in methods for culture of various tumor cells in the tumor vasculature networks, which can be followed by an expanded and more detailed study of invasion and metastatic behavior in the presence of extracellular matrix, endothelial cells, co-culture of tumor cells and immune cells (macrophages, etc.), or the like. Protocols for real-time analysis of circulation, growth, and migration of tumor cells in the presence of extracellular matrix such as matrigel and endothelial cells can be used with the device. Migration, invasion, and metastasis patterns can be quantified in the microfluidic network. Nanopolymer-based drug delivery for siRNA or other anti-tumor therapeutics can be studied in the device. The device can be used with: (a) bioMEMS development, hemodynamic, and cellular analysis; (b) microcirculation, tumor biology, targeted therapy, and oncology; (c) tumor migration and drug development; and (d) nanoparticles-based tumor drug delivery. Also, the device can be used with assay protocols to study targeted drug delivery to the vascular endothelial layer, which can be important in the metastasis studies. The device can be used to characterize the mechanisms of metastasis process, and in drug discovery where it can be used to measure the effect of inhibitors of metastasis. Thus, the device can be used in cancer research and drug delivery.

Accordingly, the device provides detailed microvascular network structures obtained from in vivo animal data patterned onto PDMS (polydimethylsiloxane) to form a plastic, disposable substrate with optical clarity and good gas permeability enabling cell culture applications. This allows one to recreate in vivo simulated environments in vitro, with similar fluidic/shear conditions and topologies. The patterns of these vessels can include plastic tissue sections that have gaps ranging from 5 μm to 15 μm that can be covered with extracellular matrices (e.g., Matrigel, Collagen) that dictate permeation from the vascular to the tissue space. Following the culture of endothelial cells to confluence on the vascular side, circulating tumor cells can be introduced in the tissue space of the chip or elsewhere (e.g., inlet). Adhesion and rate of migration and invasion of the tumor cells into tissue space can be captured in real-time by scanning the entire network using automated tracking. Growth of tumor cells in selected pockets of the tissue area can enable studies on distal tumor adhesion, migration, invasion, and eventually metastasis. Thus, the device can include a metastatic device and assay: In vitro microfluidic metastasis chip with anatomically realistic features based on in vivo microvascular network images and 5- to 15-μm (e.g., 9 micron) leaky gaps; automated protocols for real-time visualization of tumor cells adhesion, migration, invasion, metastasis, and drug delivery; and customized software to analyze experimental data generated on-chip.

In one embodiment, the device can provide improvements in: Integrated tumor metastasis device; flow and morphologically realistic environment; quantitative real-time visualization; ability to screen new anti-tumor therapeutics; and reduced reagent/cell use and disposable chips. In one example, a sample reagent savings for the microvascular network in comparison with a parallel plate flow chamber for studying metastasis is shown in Table 1.

TABLE 1

Typical Savings for a Microvascular Network Compared to a Parallel Plate Flow Chamber.

| Adhesion Device | Reagent Volume (μl) | Number of Particles/ Experiment | Dead Volume Tubing (μl) |
| --- | --- | --- | --- |
| Typical Flow Chamber | 50-2000 | 5E+05 | 32.0 |
| Microvascular Network | 1 | 5E+02 | 3.0 |

The device can be used to quantitatively study adhesion of tumor cells in the microcirculatory network. Adhesion is often an overlooked step during metastasis and this study is the first of its kind to examine adhesion of tumor cells in an in-vivo-like environment complete with flow and morphology. Studies with cell/particle adhesion within the microcirculatory environment were heretofore complex and spatially dependent, and particles are found to preferentially adhere in bifurcations. As such, studies of receptor-mediated adhesion as opposed to steric trapping can be performed with the device.

The networks are morphologically complex and not suitable for idealized, analytical treatment. As a result, we have previously developed computational models for study of fluid and particle/cell motion in the networks. The procedure is described here in brief. Computational mesh for the microvascular network is created by importing network layouts into the mesh generation module of CFD-ACE+ software. This software, a general-purpose Computational Fluid Dynamics (CFD) code based on the Finite Volume Method (FVM) is used to discretize and solve the governing fluidic and particle equations. A three-dimensional hybrid mesh comprising of hexahedral and prismatic elements can be generated to show the velocity profiles highlighting the fact that nanoparticles distribution is significantly different than microparticle distribution in the networks (see incorporated applications and provisional). These simulation results can help in analysis of cell flux and adhesion data in the network.

The methods can also compare data with the device with a database of simulations with descriptions of fluidic shear and particle flux conditions in various regions of the networks. These data can be used in the interpretation of results. Internal data has provided an excellent agreement between experimental and simulation results of perfusion in the network. As such, transient perfusion studies comparing experimental and simulation results can be performed with the SMN.

The device can be used to study non-viral, functionalizable vectors for the delivery of therapeutic genes. Also functionalized polymeric systems to deliver siRNA into tumor cells can be studied to obtain a high degree of specific knockdown of target transcripts. Use of these kinds of polymers and siRNA can help develop therapeutics to combat metastasis. The device may also be used for drug screening and research on cancer, angiogeneis, inflammation, wound healing, radiation damage, and the like.

In one embodiment, the device can include: a microfludic chip with embedded microvascular networks and tissue space to study metastasis; a microfluidic chip with areas defining tissue and vascular space; a microfluidic chip with areas defining tissue and vascular space separated by a porous (e.g., 1-30 µm) wall with multiple gaps in the wall defining the pores; a microfluidic chip with areas defining vascular and tissue space capable of growing various types of cells; a microfluidic chip with areas defining vascular and tissue space capable of growing multiple type of cells in co-culture; a microfluidic chip with areas defining vascular and tissue space capable of growing tumor cells; a microfluidic chip with areas defining vasculature capable of having a vascular matrix; a microfluidic chip with areas defining a tissue space capable of having extracellular matrix or basement membranes (e.g., matrigel, collagen, etc.); a microfluidic chip for use in studying real-time circulation of cells and adhesion of cells, such as metastatic cells; and a microfluidic chip for drug screening. The device can be used with an integrated metastatic assay to study circulation, adhesion, migration, and invasion with physiological flow in tissue spaces and channels derived from in vivo structures. The migration of cells can be between gaps in walls, which gaps can vary in size. The studies can be quantitative and in real time with visualization with a resolution for single cells. The cells can be in a 3-D matrix. The cells can be adherent or suspension cells. The gradients in the SMN can be multi-directional. The device can be used in a fully automated system.

In one embodiment, a cell culture device can include: at least one internal chamber configured for an internal cell culture; at least one fluid channel bordering the internal chamber that is configured for a channel cell culture; at least one wall separating the internal chamber and at least one fluid channel having gaps that fluidly couple the internal chamber with the at least one fluid channel; and at least one metastatic cancer cell in the at least one internal chamber, at least one fluid channel, or gap therebetween. In one aspect, the internal chamber can include a first cell type and the at least one fluid channel includes a second cell type. In one aspect, the at least one internal chamber and at least one fluid channel are modeled from physiological features. In one aspect, a first internal chamber includes a cancerous cell type and a first fluid channel includes an endothelial cell type, and a second internal chamber is devoid of the cancerous cell type.

In one embodiment, a cell culture system can include: a device in accordance with one of the embodiments; and means for assaying metastasis of the at least one metastatic cancer cell.

In one embodiment, a method of assaying metastasis can include: providing a device of one of the embodiments; introducing the at least one metastatic cancer cell into the at least one internal chamber or at least one fluid channel; and monitoring metastasis of the at least one metastatic cancer cell. In one aspect, the at least one metastatic cancer cell is introduced into a first internal chamber and cultured. In one aspect, the method includes detecting escape of the at least one metastatic cancer cell from the first internal chamber into the at least one fluid channel. In one aspect, the method includes detecting migration of the at least one metastatic cancer cell through the at least one fluid channel. In one aspect, the method includes detecting adhesion of the at least one metastatic cancer cell to a coating on the at least one fluid channel. In one aspect, the coating includes endothelial cells. In one aspect, the method includes detecting invasion of the at least one metastatic cancer cell into a second internal chamber from the at least one fluid channel. In one aspect, the method includes visualizing metastasis of the at least one metastatic cancer cell with a visualization device.

In one embodiment, the method includes: modulating shear force of fluid flow in the at least one fluid channel; and assaying impact of shear forces on metastasis.

In one embodiment, the method includes: introducing an immunological substance into the at least one fluid channel; and assaying impact of the immunological substance on metastasis.

In one embodiment, the method includes: introducing an agent into the device; and screening the agent for anti-metastasis properties.

In one embodiment, the method includes: introducing the at least one metastatic cancer cell into the first internal chamber and culturing the at least one metastatic cancer cell; detecting escape of the at least one metastatic cancer cell from the first internal chamber into the at least one fluid channel; detecting migration of the at least one metastatic cancer cell through the at least one fluid channel; detecting adhesion of the at least one metastatic cancer cell to endothelial cells on the at least one fluid channel; and detecting invasion of the at least one metastatic cancer cell into a second internal chamber from the at least one fluid channel.

In one embodiment, the method includes: introducing the at least one metastatic cancer cell into the at least one fluid channel; detecting migration of the at least one metastatic cancer cell through the at least one fluid channel; detecting adhesion of the at least one metastatic cancer cell to endothelial cells on the at least one fluid channel; and detecting invasion of the at least one metastatic cancer cell into an internal chamber from the at least one fluid channel.

In one embodiment, at least one wall separating the internal chamber and at least one fluid channel has gaps that are coated with a matrix material.

In one embodiment, the method includes culturing a tissue cell in at least one internal chamber, the tissue cell excluding a metastatic cancer cell.

EXPERIMENTAL

FIGS. 1A-1D show devices with SMNs that have physiological features. This process of creating microvascular networks on a chip from the network topology data can be described to include: capturing in vivo images; processing the in vivo images with a database of images; viewing the structure of the in vivo images with a graphical interface (GIS-based method, ANET); using a programming interface to obtain a simulated vascular network that includes the physiological features of the vascular network; and creating the SMN with flow channels and tissue spaces defined, where numbers can be applied to indicate vessel identification, node exits, and entrances can be defined; and arrows can be used to indicate the direction of blood flow. This can be applied to the lymphatic system also. The digitized images can be converted into a mask using a standard MEMS technique before making the PDMS-based microfluidic channels. Devices from a microvascular network of hamster cremaster muscle in vivo ranging from 10-100 μm have been constructed. The in vivo images can be obtained from a database.

The device can use both a metastatic (e.g., MDA-MB-231 (ATCC # HTB-26™) and non-metastatic cell line (e.g., MCF-7 (ATCC # HTB-22™) for evaluation of shear survivability. The MDA-MB-231 cell line can be cultured at 37° C. with 5% $CO_2$ in Dulbeco minimum essential medium (DMEM) supplemented with 10% fetal bovine serum, 2 mmol/L glutamine, and 1% penicillin-streptomycin-neomycin antibiotics. Confluent cells can be regularly sub-cultured in the ratio of 1:3. Similarly, MCF-7 cell line can be cultured at 37° C. and 5% $CO_2$ in Eagle's minimum essential medium supplemented with 0.01 mg/ml of bovine insulin and 10% fetal bovine serum. Viability determination can be made using trypan blue exclusion assay of cells collected at the end of the experiment.

Tumor cells at a concentration of 10^6/ml can be used for all the studies. An aliquot can be assayed for cell viability using the trypan blue procedure. Following initial viability calculation, the tumor cells can be injected in a channel for circulation using a peristaltic pump with flow rates adjusted to the corresponding shear rates. Varying shear rates (e.g., 250, 500 and 1000 $sec^{-1}$) and time (e.g., four hours, 12 hours, and 24 hours) can be used. The shear rates are based on higher end of shear rates observed in vivo in the microvasculature. 24-hour time point is chosen as the last time point as we do not want the outcome to be contaminated with cell division because normal cells typically divide in 48 to 72 hours and tumor cells divide more rapidly. Temperature (e.g., 37° C.), humidity, and gas at 5% $CO_2$ can be kept constant within the incubation chamber. At the end of the respective time points, the tumor cells can be collected from the device by flushing the device with cell free media. The cells can be centrifuged and re-suspended in cell media prior to performing a viability assay using trypan blue. Table 2 summarizes an experimental plan. Number of viable cells before and after treatment can be compared to see if the cells are being damaged following the shear treatment. A curve of shear rate versus viability can be generated. Each of the experiments can be repeated three times to yield data for statistical analysis.

TABLE 2

Experimental Plan for Viability Studies in the Network

| Cell Type | Shear Rate (sec-1) | Time Points (hr) |
|---|---|---|
| MDA-MIB-231 | 250, 500 and 1000 | 4, 12 and 48 |
| MCF-7 | 250, 500 and 1000 | 4, 12 and 48 |

Protocols for successful growth of endothelial cells in the microfluidic networks can be used. Time-lapse images can show confluent endothelial cell growth in the network. In addition, long-term cell culture and adhesion studies can be performed on the activated endothelium cells. It is known that endothelial cells upregulate ICAM-1 significantly following treatment with cytokines. Endothelial cells can be activated with TNF-α for four and 24 hours, respectively, in the network. Following activation, fluorescent particles coated with antibody to ICAM-1 and IgG particles (control) can be injected into the network. Particles bound can be quantified using fluorescence microscopy. Data (not shown) highlights the increase in particle adhesion at 24 hours compared to four hours. The procedures developed here for the culture of cells and visualizing and quantitating adhesion can be employed for metastasis.

Study of Tumor Cell Adhesion in Network

The device can be used to study adhesion of tumor cells in the microcirculatory network. Adhesion is often an overlooked step during metastasis and study tumor adhesion in an in-vivo-like environment complete with flow and morphology. It is known that cell/particle adhesion within the microcirculatory environment is complex and spatially dependent, and particles are found to preferentially adhere in bifurcations. The studies can include receptor-mediated adhesion as opposed to steric trapping in bifurcations.

The device can be placed on an automated stage (Bioprecision, LEP Ltd, Hawthorne, N.Y.) on a microscope (Nikon TE 2000) equipped with a Retiga Exi Cooled Camera. Sterile phosphate buffer saline can be injected into the network at a flow rate of 10 μl/min for 10 minutes using a syringe pump. Following this, poly-D-lysine (Millipore, Billerica, Mass.) can be injected at a concentration of 100 μg/ml at a flow rate of 10 μl/min for five minutes. Solution can be allowed to stand in the network overnight at 4° C. Sterile media can then be injected into the network and the device can be kept in the incubated chamber for allowing equilibrium with cell culture media. Tumor cell adhesion can be studied using a circulation loop.

Figure 3A:
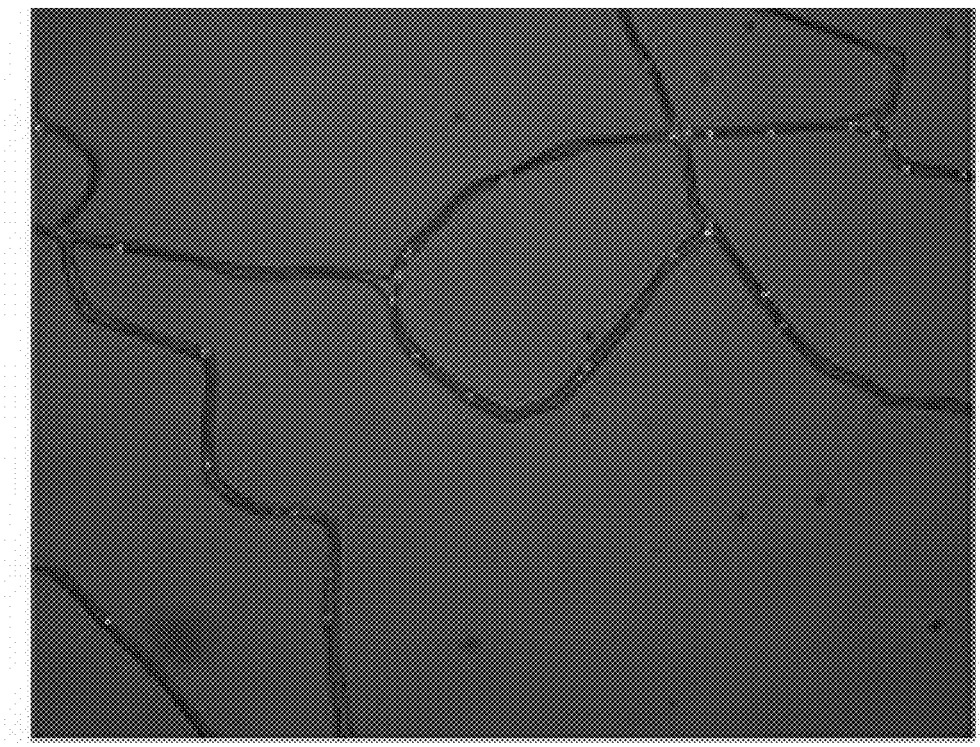
FIG. 3A includes an image of anti-P-selectin antibody-coated particles binding to P-selectin in a portion of an SMN network.
Figure 3B:
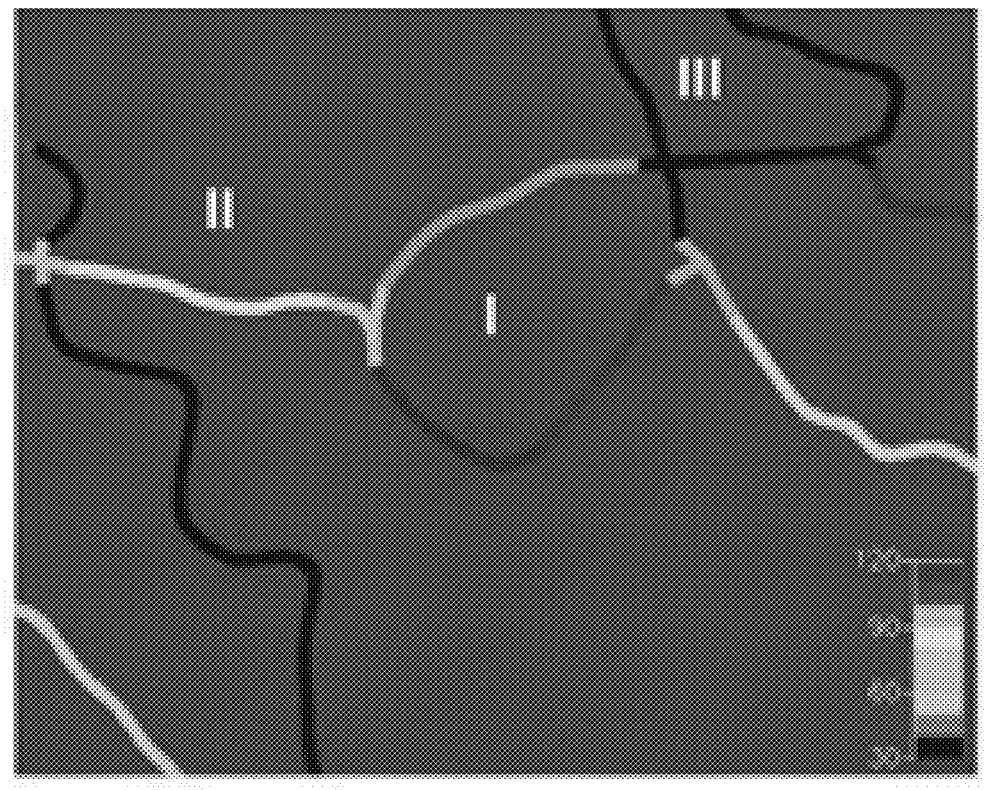
FIG. 3B includes an image of shear variation in an SMN Network, with I being moderate perfusion with low shear; II being high perfusion and high shear; and III being low perfusion, low shear.
Figure 3C:
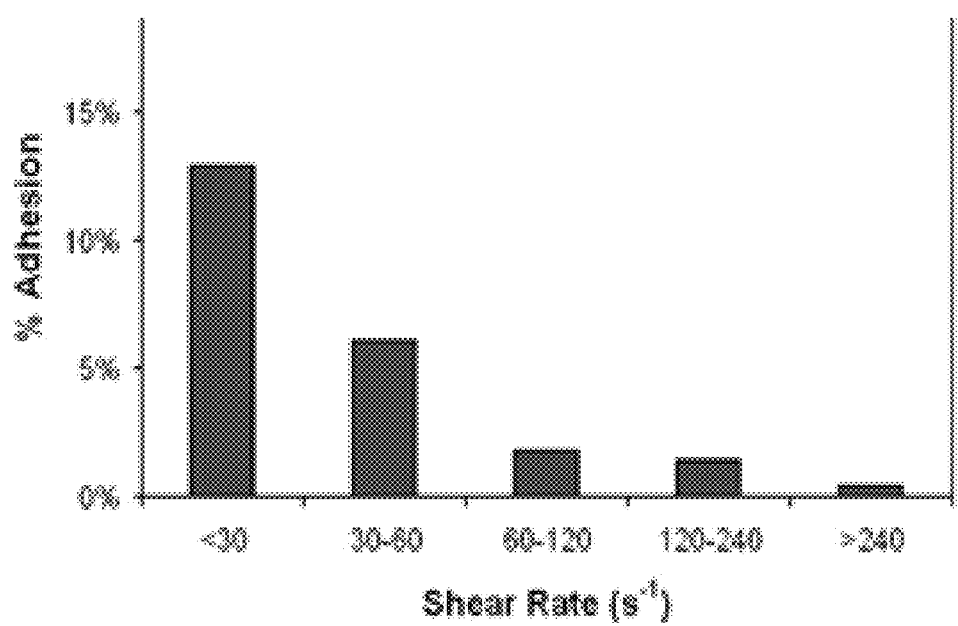
FIG. 3C includes a graph that shows particle adhesion versus shear rate in the SMN network.

Tumor cells at a concentration of 10^6 cells/ml can be perfused into the chamber at a flow rate corresponding to shear rate of 250, 500, and 1000 sec-1 for two time points 30 minutes and four hours, respectively, using a peristaltic pump connected via a two-input perfusion manifold (Harvard Apparatus, MA). Nikon Elements software can be used to automatically control the stage, camera, and the timing for image acquisition. The software can scan the entire network every 15 minutes to make an entire video montage of the network using a 4× Phase contrast magnification. At the end of four hours, the flow can be switched to a cell free media wash using the second input connection of the perfusion manifold and a syringe pump (Harvard Apparatus, Holliston, Mass.). Following the wash step, the network can be scanned to observe the adhered cells. FIGS. 3A-3C show experimental data of anti-P-selectin antibody-coated particles binding to P-selectin-coated microvascular networks. It is also seen that on mapping the shear rates from the simulation runs (FIG. 3B), one can predict the behavior of the adhesion patterns observed. Comparison of the shear rate map and particle adhesion data in the network can allow the creation of a shear rate curve (FIG. 3C) for the tumor cells. It can also determine if these cells can form strong bonds with the endothelium and maintain them in order to migrate into the tissue. Table 3 summarizes sample experiments that can be conducted. Cells can be visualized via phase contrast microscopy, or visualized using live cell fluorescence dyes such as SYTO 16.

TABLE 3

Adhesion experiments experimental summary

| Cell Line | Shear Rate (sec-1) | Experimental Run |
|---|---|---|
| MDA-MIB-231 | 250, 500 and 1000 | Real time for 30 minutes and 4r |
| MCF-7 | 250, 500 and 1000 | Real time for 30 minutes and 4r |

Migration Studies of Tumors in Network

Additionally, the quantitative migrational potential of tumor cells can be studied in the networks of the device. Migration can be captured real time and physiological flow conditions can be present to determine the migration patterns. In addition, this study can distinguish clearly the migrated cells as the cells in the tissue section of the network can contain only migrated cells. Tumor cells can be allowed to adhere to the network using the protocol mentioned above. Following adhesion, the cell media in the network can be replaced with serum free media. The serum free media can be maintained for 24 hours with circulating perfusion at average physiological shear rate of 120 sec-1, which is commonly found in post-capillary venules and the sites of adhesion. Following the starvation of the cells with serum, the tissue sections of the network can be filled with cell media containing 20% serum. The network can be repeatedly scanned and imaged as before every 30 minutes for 24 hours using Nikon Elements automated feature. Any cell that has left the vessel area and migrated into the tissue area can be easily seen with the images. At the end of the respective time point the individual images can be merged together to create a time lapse image to quantify the number of cells that have migrated into the tissue area. A plot of cells migrated versus the local shear rate can be generated. In addition, the geometric features of the adhesion sites can be noted to allow for distinguishing between shear only or shear and geometry-based adhesion. Phase contrast microscopy can be used, or fluorescent live cell dyes for visualization.

A static migration experiment can also be performed in these networks. In these, the cells can be injected into the networks and allowed to settle and attach to the surface for four hours. Following attachments, the cell media can be replaced with serum free media. The cells can be allowed to starve for 24 hours in this media. Following 24 hours, cell media containing 20% serum can be injected into the tissue area of the network. These networks can then be scanned every 30 minutes for 24 hours to take time-lapse images. At the end of 24 hours, the images can be visualized to observe migrated cells. The migration data in the absence of fluidic conditions can then be compared with that of fluidic conditions to extract the difference between the two procedures (Table 4). Transient rate of migration of the cells can also be quantified by measuring the distance traveled in the time period.

TABLE 5

Migration Experiments Experimental Summary

| Cell Line | Static Condition | Flow Condition |
|---|---|---|
| MDA-MIB-231 | Real time for 24 hr | Real time for 24 hr |
| MCF-7 | Real time for 24 hr | Real time for 24 hr |

Invasion Studies on Tumors in Network with Matrigel

A key step for the tumors to start proliferating at the new site of migration is to invade into the basement membrane and then set up new colonies in the tissue. The objective of this study can be to determine the invasive patterns of the tumors in the network using matrigel coating in the tissue area of the section. The experiment can use matrigel at desired locations in the network of the device rather than the entire network. These desired locations can be determined based on the adhesion patterns in the networks. Tissue locations near the vessels with the highest number of cell adhesions in decreasing order can be used. Matrigel (BD Biosciences, Bedford, Mass.) can be obtained and mixed to a final concentration of 1 mg/ml in serum free cold media. The matrigel solution (volume dependent upon tissue area) can then be injected into the prescribed tissue areas of the network in a clean environment (Sterilgard Type II A2 biosafety cabinet, Baker, Sanford, Me.). A small amount of vacuum can be applied in the channels to aid in movement of the matrigel solution into the gaps for five minutes. Following vacuum treatment, the matrigel solution can be quickly pipetted out from the tissue area leaving the matrigel in the gaps intact. The device can be kept inside the biosafety cabinet for one hour for the matrigel to polymerize. Cells can then be injected into the device using the protocols mentioned above at a shear rate of 120 sec-1. Serum rich (20%) media can then be injected into the tissue space. As before, the stage can scan the entire network for every 30 minutes for 24 hours to visualize the invasion of the tumor cells into the tissue space. The invasion capability of the tumor cells in two locations can then be compared with each other to arrive at shear rate versus invasion map. A similar experiment can be performed using the non-metastatic tumor cells MCF-7 for comparison purposes.

Nanoparticle/Drug Screening for Control of Metastasis

Figure 4A:
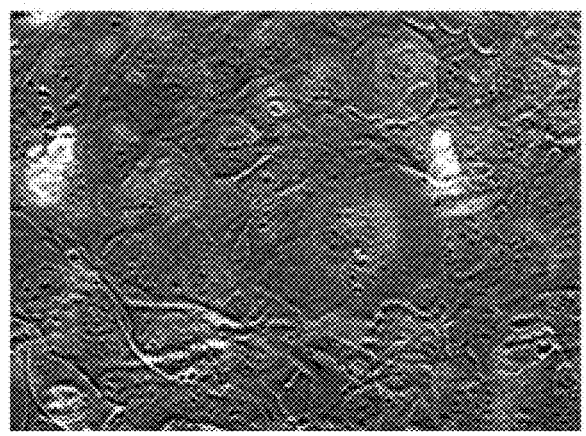
FIG. 4A shows low magnification images.
Figure 4B:
FIG. 4B shows high magnification images showing polymers and the cell nucleus.
Figure 4C:
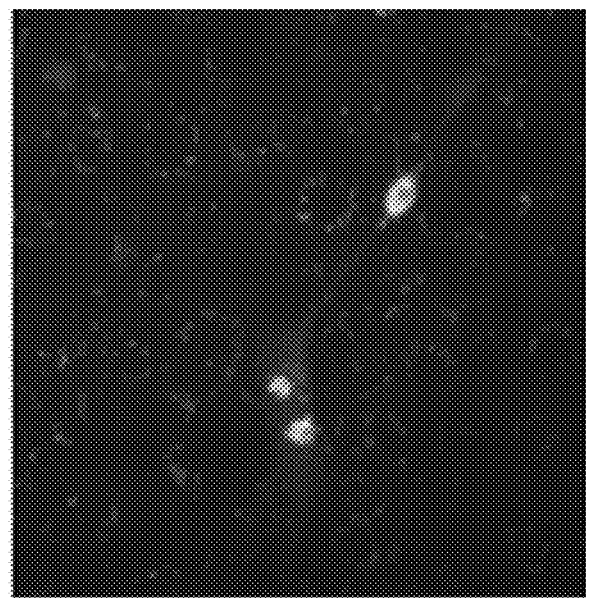
FIG. 4C shows GFP expression.

The objective of this study is to use the device as a screening tool for next generation anti-metastatic molecular therapies (e.g., gene, siRNA, etc). We can demonstrate the ability to deliver a putative therapeutic agent (e.g., simulated by GFP encoding gene) while the tumor cell is in circulation and follow/compare its impact on metastatic behavior. GFP labeled nanopolymers (e.g., 10 µg/ml) can be injected into the networks following adherence of the tumor cells in the network. The circulation loop can be run for 24 hours in the incubation chamber. The entire network can be scanned and imaged as before every two hours. The GFP expression profiles can be quantified in the network. The cells expressing GFP and their location in the network and the corresponding local shear conditions can be characterized. FIGS. 4A-4C show results from an experiment on nanoparticle uptake by endothelial cells and subsequent GFP expression, which shows nanoparticle uptake and GFP expression on bovine aortic endothelial cells. FIG. 4A shows low magnification images. FIG. 4B shows high magnification images showing polymers and the cell nucleus. FIG. 4C shows GFP expression.

One skilled in the art can appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as can be apparent to those skilled in the art. Functionally equivalent methods and apparatuses within the scope of the disclosure, in addition to those enumerated herein, can be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In one embodiment, the present methods can include aspects performed on a computing system. As such, the computing system can include a memory device that has the computer-executable instructions for performing the method. The computer-executable instructions can be part of a computer program product that includes one or more algorithms for performing any of the methods of any of the claims.

In one embodiment, any of the operations, processes, methods, or steps described herein can be implemented as computer-readable instructions stored on a computer-readable medium. The computer-readable instructions can be executed by a processor of a wide range of computing systems.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle can vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It can be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It can be further understood by those within the art that if a specific number of an introduced claim recitation is intended, such an intent can be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art can recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It can be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" can be understood to include the possibilities of "A" or "B" or "A and B."

In addition, where features or aspects of the disclosure are described in terms of Markush groups, those skilled in the art can recognize that the disclosure is also thereby described in terms of any individual member or subgroup of members of the Markush group.

As can be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As can also be understood by one skilled in the art all language such as "up to," "at least," and the like include the number recited and refer to ranges which can be subsequently broken down into subranges as discussed above. Finally, as can be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it can be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

This patent document incorporates by specific reference in their entirety the following patents and patent applications: U.S. Pat. Nos. 7,725,267; 8,355,876; 8,175,814; 8,380,443; 8,417,465; 8,589,083; U.S. 2010/0227312; PCT/US2013/072081; U.S. 2013/0101991; and U.S. 2013/0149735. These applications provide background and state of the art as well as definitions for terms of art.

This patent document incorporates by specific reference in their entirety co-filed applications that claim priority to the same provisional application 61/775,158 filed Mar. 8, 2013, which co-filed applications include: C1478.10020US02 (Attorney's authorized to include serial number once known); C1478.10020US03 (Attorney's authorized to include serial number once known); and C1478.10020US04 (Attorney's authorized to include serial number once known).

The invention claimed is:

1. A method of assaying metastasis, the method comprising:
providing a cell culture device comprising:
at least one first internal chamber configured for an internal cell culture;
a first fluidic flow channel network fluidly coupled with the at least one first internal chamber, the first fluidic flow channel network comprising:
at least one first fluid flow channel bordering and surrounding the at least one first internal chamber that is configured for a channel cell culture, each first fluid flow channel having a single first fluid flow inlet and single first fluid flow outlet and being continuous between the single first fluid flow inlet and single first fluid flow outlet;
at least one first wall separating the at least one first internal chamber and the at least one first fluid flow channel, the at least one first wall having first gaps that fluidly couple the at least one first internal chamber with the at least one first fluid flow channel, wherein each first wall is continuous from the single first fluid flow inlet and single first fluid flow outlet;
at least one second fluid flow channel bordering and surrounding the at least one first fluid flow channel such that the at least one first fluid flow channel is between the at least one second fluid flow channel and at least one first internal chamber, each second fluid flow channel having a single second fluid flow inlet and single second fluid flow outlet and being continuous between the single second fluid flow inlet and single second fluid flow outlet;
at least one second wall separating the at least one first fluid flow channel and at least one second fluid flow channel, the at least one second wall having second gaps that fluidly couple the at least one first flow fluid channel and at least one second fluid flow channel, wherein each second wall is continuous from the single second fluid flow inlet and single second fluid flow outlet;
introducing at least one cancer cell into the at least one first internal chamber or first fluidic flow channel network; and
monitoring metastasis of the at least one cancer cell.

2. The method of claim 1, wherein the at least one cancer cell is introduced into the at least one first internal chamber and cultured.

3. The method of claim 2, comprising detecting escape of the at least one cancer cell from the at least one first internal chamber into the first fluid flow channel network.

4. The method of claim 1, comprising detecting migration/invasion of the at least one cancer cell through the first fluid flow channel network.

5. The method of claim 1, comprising detecting adhesion of the at least one cancer cell to a coating on the first fluidic flow channel network.

6. The method of claim 5, wherein the coating includes endothelial cells or matrices.

7. The method of claim 1, comprising detecting invasion of the at least one cancer cell into a second internal chamber from the first fluidic flow channel network.

8. The method of claim 1, comprising visualizing metastasis of the at least one cancer cell with a visualization device.

9. The method of claim 1, comprising:
modulating shear force of fluid flow in the first fluidic flow channel network; and
assaying impact of shear forces on metastasis.

10. The method of claim 1, comprising:
introducing an immunological substance into the first fluidic flow channel network; and
assaying impact of the immunological substance on metastasis.

11. The method of claim 1, comprising:
introducing an agent into the cell culture device; and
screening the agent for anti-metastasis properties.

12. The method of claim 1, comprising:
introducing the at least one cancer cell into the at least one first internal chamber and culturing the at least one cancer cell;
detecting escape of the at least one cancer cell from the at least one first internal chamber into the first fluidic flow channel network;
detecting migration of the at least one cancer cell through the first fluidic flow channel network;
detecting adhesion of the at least one cancer cell to endothelial cells on the first fluidic flow channel network; and
detecting invasion of the at least one cancer cell into a second internal chamber from the first fluidic flow channel network.

13. The method of claim 1, comprising:
introducing the at least one cancer cell into the first fluidic flow channel network;
detecting migration of the at least one cancer cell through the first fluidic flow channel network;
detecting adhesion of the at least one cancer cell to endothelial cells on the first fluidic flow channel network; and
detecting invasion of the at least one cancer cell into the at least one first internal chamber or a second internal chamber from the first fluidic flow channel network.

14. The method of claim 1, wherein at least one wall separating the internal chamber and the first fluidic flow channel network has gaps that are coated with a matrix material.

15. The method of claim 1, comprising culturing a tissue cell in at least one internal chamber, the tissue cell excluding a cancer cell.

16. The method of claim 1, wherein the at least one first internal chamber, at least one first fluid flow channel, and at least one second fluid flow channel are modeled from physiological features and include a synthetic microvascular network.

17. The method of claim 1, the cell culture device comprising:
- at least one third fluid flow channel bordering and surrounding the at least one second fluid flow channel such that the at least one second fluid flow channel is between the at least one third fluid flow channel and at least one second fluid flow channel, each third fluid flow channel having a single third fluid flow inlet and single third fluid flow outlet and being continuous between the single third fluid flow inlet and single third fluid flow outlet;
- at least one third wall separating the at least one second fluid flow channel and the at least one third fluid flow channel, the at least one third wall having third gaps that fluidly couple the at least one second fluid flow channel and at least one third fluid channel, wherein each third wall is continuous from the single third fluid flow inlet and single third fluid flow outlet; and
- at least one fourth wall bordering and surrounding the at least one third fluid flow channel, wherein the at least one fourth wall is a non-porous external wall.

18. The method of claim 1, comprising flowing a fluid through the first fluidic flow channel network.

19. The method of claim 1, wherein the provided cell culture device comprises:
- a second internal chamber devoid of a cancer cell culture, the second internal chamber being fluidly coupled to the first internal chamber via a second fluidic flow channel network that is fluidly coupled with the first fluidic flow channel network, the second fluidic flow channel network comprising:
  - at least one third fluid flow channel bordering and surrounding the second internal chamber that is configured for a channel cell culture, each third fluid flow channel having a single third fluid flow inlet and single third fluid flow outlet and being continuous between the single third fluid flow inlet and single third fluid flow outlet;
  - at least one third wall separating the second internal chamber and at least one third fluid flow channel, the at least one third wall having third gaps that fluidly couple the second internal chamber with the at least one third fluid flow channel, wherein each third wall is continuous from the single third fluid flow inlet and single third fluid flow outlet;
  - at least one fourth fluid flow channel boarding and surrounding the at least one third fluid flow channel such that the at least one third fluid flow channel is between the at least one fourth fluid flow channel and second internal chamber, each fourth fluid flow channel having a single fourth fluid flow inlet and single fourth fluid flow outlet and being continuous between the single fourth fluid flow inlet and single fourth fluid flow outlet;
  - at least one fourth wall separating the at least one third fluid flow channel and at least one fourth fluid flow channel, the at least one fourth wall having fourth gaps that fluidly couple the at least one third flow fluid channel and at least one fourth fluid flow channel, wherein each fourth wall is continuous from the single fourth fluid flow inlet and single fourth fluid flow outlet, the method comprising:
- monitoring metastasis of the at least one cancer cell into the second fluidic flow channel network and/or second internal chamber.

20. The method of claim 19, wherein the first internal chamber and second internal chamber are fluidly coupled through fluid coupling of the at least one first fluid flow channels and second fluid flow channels to the at least one third fluid flow channels and fourth fluid flow channels.

* * * * *